US008006516B2

(12) United States Patent
Ashton

(10) Patent No.: US 8,006,516 B2
(45) **Date of Patent: *Aug. 30, 2011**

(54) TONGUE AND MOUTH STUD FOR DISPENSING A SUBSTANCE

(76) Inventor: Wesley Scott Ashton, Lorton, VA (US)

( * ) Notice: Subject to any disclaimer, the term of this patent is extended or adjusted under 35 U.S.C. 154(b) by 1513 days.

This patent is subject to a terminal disclaimer.

(21) Appl. No.: 10/697,083

(22) Filed: Oct. 31, 2003

(65) Prior Publication Data

US 2004/0089022 A1 May 13, 2004

Related U.S. Application Data

(63) Continuation-in-part of application No. 09/881,806, filed on Jun. 18, 2001, now Pat. No. 6,675,613.

(51) Int. Cl.

| | |
|---|---|
| ***A61K 9/20*** | (2006.01) |
| ***A61J 7/00*** | (2006.01) |
| ***A61M 31/00*** | (2006.01) |
| ***A61M 35/00*** | (2006.01) |
| ***A44C 7/00*** | (2006.01) |

(52) U.S. Cl. ............................. 63/12; 604/290; 424/435

(58) Field of Classification Search ................... 63/1.14, 63/1.15, 12; 40/300, 301; 119/655; 424/435, 424/400, 440, 484, 486
See application file for complete search history.

(56) References Cited

U.S. PATENT DOCUMENTS

| | | | | |
|---|---|---|---|---|
| 363,030 A | | 5/1887 | Wessel | |
| 511,952 A | | 1/1894 | Hubash | |
| 2,568,207 A | | 9/1951 | Spicher | |
| 3,500,829 A | | 3/1970 | Abramowitz | |
| 3,503,127 A | * | 3/1970 | Kasdin et al. | 433/199.1 |
| 3,600,807 A | * | 8/1971 | Sipos | 433/167 |
| 3,754,332 A | * | 8/1973 | Warren, Jr. | 433/217.1 |
| 3,943,928 A | * | 3/1976 | Lariccia et al. | 604/57 |
| 4,020,558 A | * | 5/1977 | Cournut et al. | 433/80 |
| 4,056,951 A | | 11/1977 | Black | |
| 4,159,631 A | * | 7/1979 | Lee | 63/1.15 |
| 4,175,326 A | * | 11/1979 | Goodson | 433/80 |
| 4,353,370 A | | 10/1982 | Evans | |
| 4,454,110 A | * | 6/1984 | Caslavsky et al. | 424/54 |
| 4,551,329 A | * | 11/1985 | Harris et al. | 424/440 |
| 4,676,752 A | * | 6/1987 | Lefkowitz | 433/229 |
| 4,681,544 A | * | 7/1987 | Anthony | 433/215 |
| 4,781,036 A | | 11/1988 | Erickson | |
| 4,785,642 A | | 11/1988 | Chin et al. | |
| 4,861,268 A | * | 8/1989 | Garay et al. | 433/229 |
| 4,943,274 A | | 7/1990 | Edwards | |
| 4,959,052 A | * | 9/1990 | Cox | 604/77 |
| 5,016,369 A | | 5/1991 | Parry | |

(Continued)

OTHER PUBLICATIONS

Perkins, C.S. et al.: A complication of tingue piercing. Br. Dent. J. 182: 147-148 (1997).

(Continued)

*Primary Examiner* — Jack W. Lavinder
(74) *Attorney, Agent, or Firm* — Griffin & Szipl, P.C.

(57) ABSTRACT

The present invention discloses a tongue and mouth stud for dispensing a substance such as a chemical, breath freshener, pleasant flavor, or medication into the mouth of a wearer. This tongue and mouth stud includes a means for dispensing a substance comprised of an internal cavity for storing and dispensing the substance contained within through one or more openings in the surface of the tongue stud that are contiguous with the internal cavity. Furthermore, the means for dispensing a substance may include a sponge positioned within the internal cavity of the mouth and tongue stud.

20 Claims, 6 Drawing Sheets

U.S. PATENT DOCUMENTS

| | | | | |
|---|---|---|---|---|
| 5,074,786 | A * | 12/1991 | Woodward | 433/80 |
| 5,090,903 | A * | 2/1992 | Taylor et al. | 433/80 |
| 5,632,163 | A | 5/1997 | Inoue | |
| 5,855,908 | A * | 1/1999 | Stanley et al. | 424/440 |
| 6,026,659 | A | 2/2000 | Kaping, Jr. | |
| 6,039,049 | A | 3/2000 | Piperato et al. | |
| 6,047,209 | A * | 4/2000 | Denny et al. | 604/21 |
| 6,167,725 | B1 | 1/2001 | Siekierski | |
| 6,244,073 | B1 * | 6/2001 | Kaping, Jr. | 63/12 |
| 6,326,022 | B1 * | 12/2001 | Katz | 424/435 |
| 6,592,860 | B1 * | 7/2003 | Levy et al. | 424/78.08 |

OTHER PUBLICATIONS

De Moor, RJG et al.: Tongue piercing and associated oral and dental complications. Endol. Dent. Traumatol. 16:232-237 (2000).

Farah, C.S. et al.: Tongue piercing: Case report and review of current practice. Aust. Dent. J. 43.387-389 (1998).

Cobb. D.S. et al.: Adhesive Composite Inlays for the Restoration of Cradled Posterior Teeth Associated with a Tongue Bar. Pract. Periodont. Aesthet. Dent. 10:453-460 (1998).

Botchway, C. et al.: Tongue piercing and asociatede tooth fracture. J. Can. Dent. Assoc. 64:803-805 (1998).

Reichl, R.B. et al.: Intraoral body-piercing: a case report. Gen. Dent. 44:346-347 (1996).

Chen, M. et al.: Tongue piercing: a new fad in body art. Br. Dent. J. 172(3):87 (1992).

Hardwood-Nuss, A.L.: The Clinical Practice of Emergency Medicine, 3rd ed. Lippincott William & Wilkins, Philadelphia, 2001, pp. 477-478.

Gorbach, S.L. et al.(eds): Infections Diseases, 2nd ed., W.B. Saunders Co., Philadelphia, 1998, pp. 510-511, 1261-1262 and 1266.

Champion, R.H. et al.(eds): Textbook of Dermatology, vol. IV, Rev. ed., Blackwell Science, Inc., Malden, MA, 1998, pp. 3019-3020.

Schmidt, B.D.: Your Child's Health: the Parent's Guide to Symptoms, Emergencies, Common Illnesses, Behavior, and School Problems, Rev ed., Bantham Books, New York, 1991, pp. 77-78, 80-82 and 524-527.

* cited by examiner

TONGUE AND MOUTH STUD FOR DISPENSING A SUBSTANCE

The present application is a continuation-in-part of U.S. patent application Ser. No. 09/881,806, filed Jun. 18, 2001, which is now U.S. Pat. No. 6,675,613 B2, both of which are incorporated herein in their entirety.

BACKGROUND OF THE INVENTION

1. Field of the Invention

The present invention pertains generally to ornamental jewelry inserted and worn by a person or animal after body piercing. More specifically, the present invention pertains to mouth and tongue studs, a type of ornamental jewelry comprised of a metal or plastic bar with removable balls at the ends that can be inserted into an artificially formed fistulous tract previously created in the mouth or tongue of the wearer. The present invention specifically improves upon the prior art mouth and tongue stud by providing a means for dispensing a substance such as chemicals, breath fresheners, pleasant flavors, or medications to the wearer.

2. Description of the Prior Art

Body piercing is a longstanding human tradition and for years many people have worn jewelry such as earrings that are inserted into an artificially created fistulous tract. In recent years, the popularity of other kinds of body pierced jewelry has grown to include nose rings, belly button rings, genital rings, and tongue studs. The typical tongue stud (600) as shown in FIG. 11 consists of a simple solid bar (610), made of metal or plastic that attaches via male threads (612) to female threads (625) of recess (623) in solid ball (620) at each end of the tongue stud (600). Each solid ball (620) is also made of metal or plastic. The shape of solid ball (620) is generally spherical although other shapes such as pyramids and square box shapes have been employed. Furthermore, the bar (610) may be straight, curved, or corkscrew in shape. When in use, the bar (610) rests in a fistulous tract (f) in the wearers tongue (T). It is noted that tongue studs may be mounted in other parts of the wearer's mouth such as the front lower lip. The bar (610) is held in place in the wearers tongue or in a wearer's lip by the solid balls (620). To place or remove the tongue stud (600), at least one of the solid balls (620) must be screwed off of the bar (610) so that the bar (610) may slide out of the fistulous tract (f). The main function of the prior art tongue stud is ornamentation. Another function of the prior art tongue stud is to enhance tactile stimulation during human sexual activities.

SUMMARY OF THE INVENTION

It is a primary object of the present invention to overcome the limitations of the prior art tongue studs as previously described.

It is a primary object of the present invention to provide an ornamental tongue stud that dispenses substances such as chemicals, breath fresheners, pleasant flavors, and/or medications to the wearer.

It is a primary object of the present invention to provide a tongue stud for enhancing human sexual activities and that dispenses substances such as chemicals, breath fresheners, pleasant flavors, and/or medications to the wearer.

The specific feature of the present invention for achieving the desired objectives is a means for dispensing a substance to the mouth, being the tongue and or sublingual regions, of the wearer during use. This means for dispensing a substance from the tongue stud is comprised of a cavity in either the bar, the balls, or both, and at least one hole in either the bar or at least one of the balls that is contiguous with the cavity so that a substance stored in the cavity may leech out of the cavity via the hole and into the wearers mouth. Clearly, the substance placed in the cavity may be solid or liquid and may comprise of a chemical, a breath freshener, a pleasant flavor, a medication, or any combination of these substances.

In a first embodiment in accordance with the present invention, a method for dispensing a substance into a mouth is provided, wherein the substance is selected from the group consisting of a breath freshener and a flavoring agent, and the method includes the steps of: (a) providing a mouth and tongue stud including a means for dispensing a substance formed in a portion of the stud, wherein the means for dispensing a substance contains the substance; (b) mounting the stud in a part of a wearer's mouth; and (c) dispensing the substance into the wearer's mouth. In a second embodiment of the present invention, the first embodiment is modified so that the substance comprises a breath freshener. In a third embodiment of the present invention, the first embodiment is modified so that the substance comprises a flavoring agent. In a fourth embodiment of the present invention, the third embodiment is further modified so the substance includes a breath freshener mixed with the flavoring agent. In a fifth embodiment of the present invention, the second embodiment is modified so that the substance includes a medication mixed with the breath freshener. In a sixth embodiment of the present invention, the third embodiment is further modified so that the substance includes a medication mixed with the flavoring agent. In a seventh embodiment of the present invention, the fourth embodiment is further modified so that the substance further includes a medication mixed with the breath freshener and the flavoring agent. In an eighth embodiment of the present invention, the first embodiment is modified so that the substance is dispensed into the wearer's mouth by dissolving the substance over time in the wearer's saliva. In a ninth embodiment of the present invention, the second embodiment is modified so that the substance is dispensed into the wearer's mouth by dissolving the substance over time in the wearer's saliva. In a tenth embodiment of the present invention, the third embodiment is modified so that the substance is dispensed into the wearer's mouth by dissolving the substance over time in the wearer's saliva.

DESCRIPTION OF THE DRAWINGS OF THE INVENTION

DESCRIPTION OF THE PREFERRED INVENTION AND EMBODIMENTS

Figure 1:
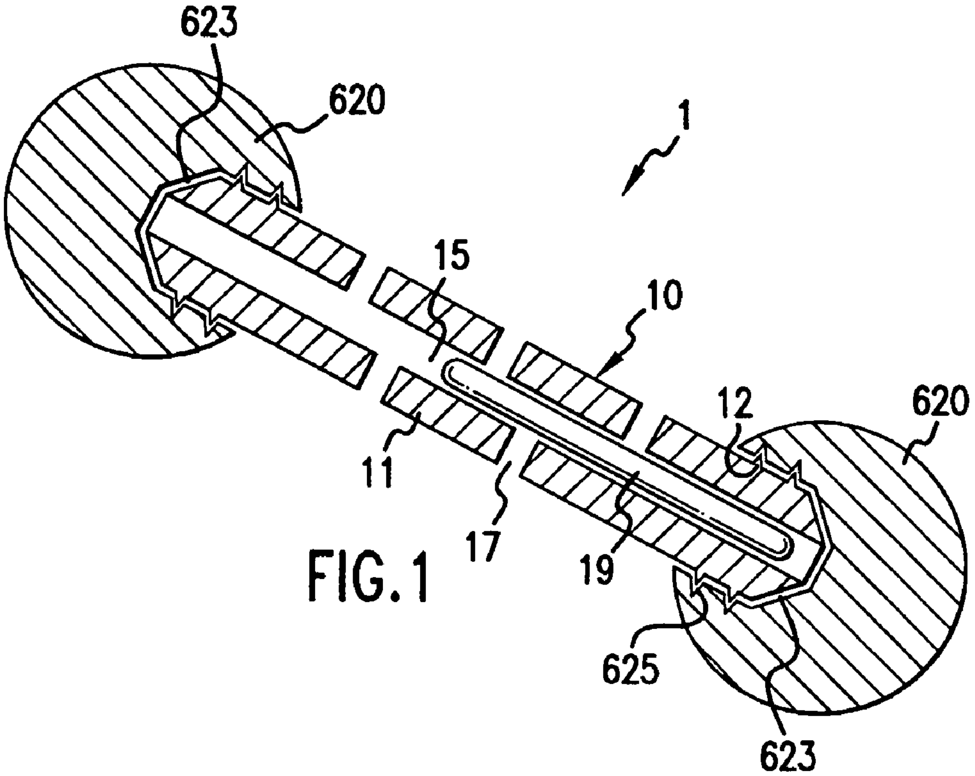
FIG. 1 illustrates a cross sectional view of tongue stud (1) having the means for dispensing a substance formed within the central bar.
Figure 2:
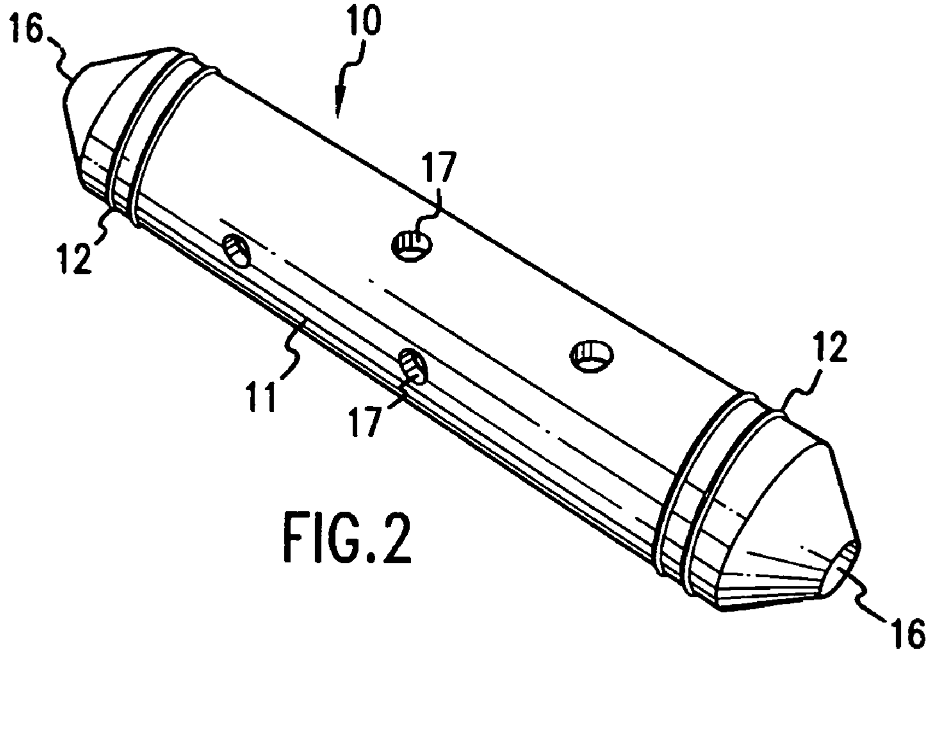
FIG. 2 illustrates a side view of the central bar of tongue stud (1).

Referring now to the drawings where like numerals indicate like parts, FIGS. 1 and 2 illustrates one embodiment of the invention, which is a tongue stud (1) comprising a central bar (10) and solid balls (620) wherein each of the solid balls (620) are attached to one of the ends of the central bar (10) by male threads (12) that screw into the female threads (625) of recess (623) in each ball (620). In this fashion, the novel tongue stud (1) is similar to the prior art tongue stud (600) and functions and is used in a similar manner. However, the novel tongue stud (1) has a means for dispensing a substance comprising a hollow core (15) having end openings (16) at either end of the central bar (10) and one or more side openings (17) in the wall (11) of the central bar (10). This means for dispensing a substance permits a substance to be placed in the hollow core (15) so that the substance may be dissolved over time by the wearer's saliva, thereby allowing the substance dissolved in the wearer's saliva to flow from the hollow core (15) through the side openings (17) and into the wearer's mouth. It is noted that the substance can be in a solid crystallized form, a gel, a foam or in a tablet form, and may consist of a chemical, breath freshener, pleasant flavor, or a medication. If the substance to be dispensed is a liquid, then a foam insert (19) can be placed inside of the hollow core (15). The foam insert provides a means for retaining the liquid so that the liquid diffuses over time out of the hollow core (15) into the wearer's mouth.

Figure 3:
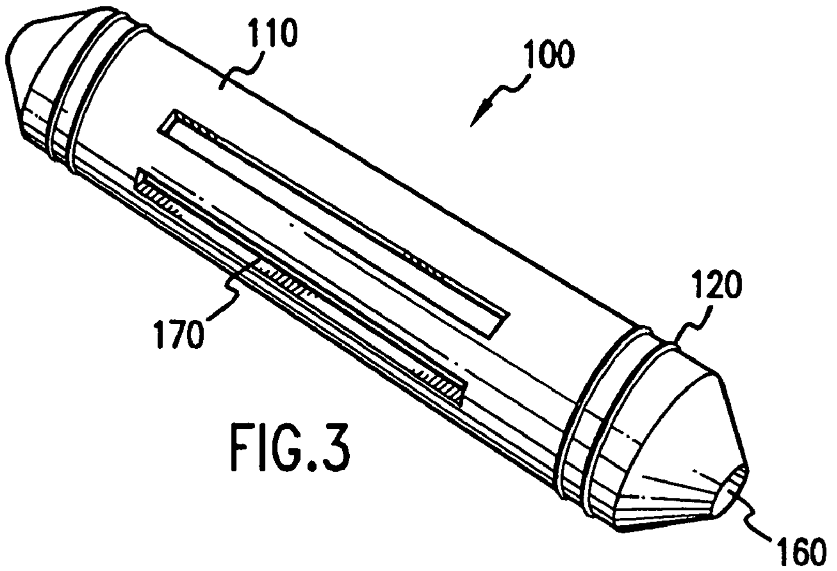
FIG. 3 illustrates a side view of a central bar having slots in place as side openings.

FIG. 3 illustrates another embodiment of the invention wherein the tongue stud would utilize the central bar (100) that has slots (170) in side wall (110). The central bar (100) also has a hollow core (not shown) contiguous with end openings (160) and side slots (170) so that any substance placed into the hollow core can flow into the mouth of the wearer via the side slots (170). Central bar (100) has male threads (120) that can threadingly engage the female threads (625) of the solid balls (620). It is noted that one alternate tongue stud embodiment comprises of central bar (100) threadingly attached to two solid balls (620), with one solid ball (620) being attached to each end of central bar (100).

Figure 4:
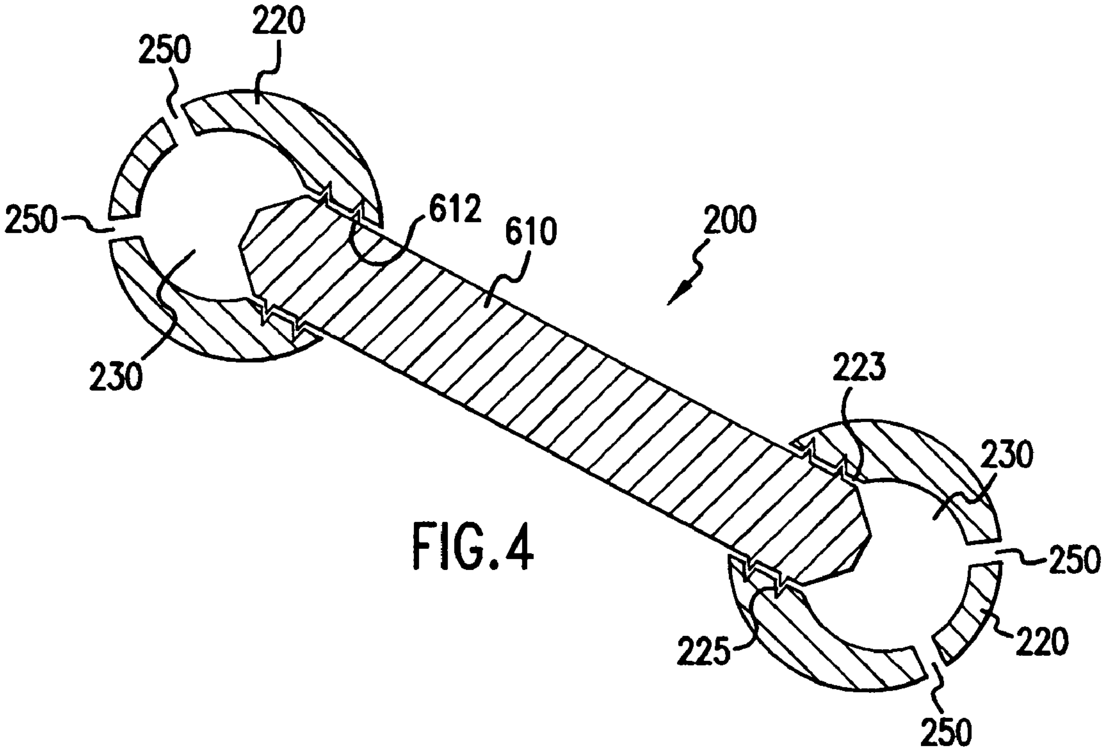
FIG. 4 illustrates a cross sectional view of tongue stud (200) having the means for dispensing a substance formed within the hollow balls.

FIG. 4 illustrates yet another embodiment of the invention. In this embodiment, tongue stud (200) comprises of solid bar (610) that threadingly engages via male threads (612) to female threads (225) of recess (223) of hollow balls (220). A hollow ball is threadingly attached to each end of solid bar (610). Each hollow ball (220) contains a central core (230) that is contiguous with the recess (223) and with at least one opening (250). In this embodiment a substance can be placed into the central core (230) of hollow ball (220) before the hollow ball (220) is threadingly engaged to the solid bar (610). Once the tongue stud (220) is placed into the wearer's mouth in the manner as described for the prior art tongue stud, then the substance in the central core (230) of the hollow balls (220) is free to dissolve in the wearer's saliva and flow from the central core (230) through the openings (250) into the wearer's mouth. It is noted that the substance can be in a solid crystallized form, a gel, a foam or in a tablet form, and may consist of a chemical, breath freshener, pleasant flavor, or a medication. If the substance to be dispensed is a liquid, then a foam insert can be placed inside of the central core (230) of each ball (220). The foam insert provides a means for retaining the liquid so that the liquid diffuses over time out of the central core (230) into the wearer's mouth. Furthermore, it is noted that each ball (220) could have only a single opening (250) or a plurality of openings (250), the number of openings (250) merely affecting the rate at which a substance can be dispensed from the tongue stud (200).

Figure 5:
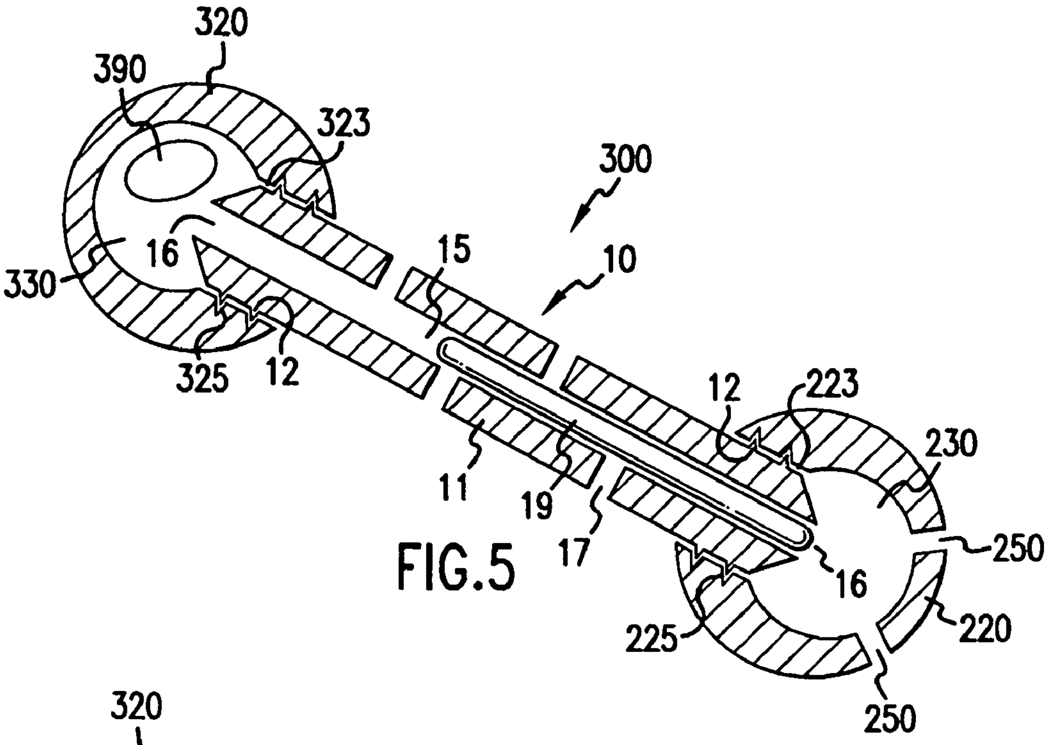
FIG. 5 illustrates a cross sectional view of tongue stud (300) having the means for dispensing a substance formed within a reservoir ball, a hollow ball, and the central bar.
Figure 6:
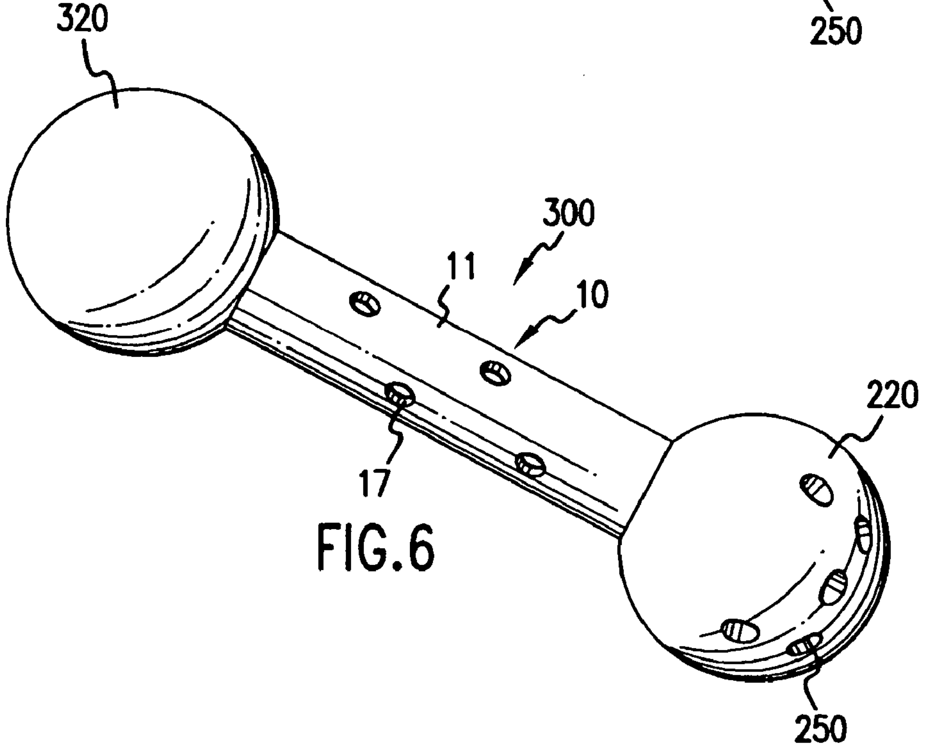
FIG. 6 illustrates a side view of tongue stud (300) shown in FIG. 5.

FIGS. 5 and 6 illustrates yet another and preferred embodiment of the invention. In this embodiment, the tongue stud (300) consists of hollow ball (220) threadingly attached via female threads (225) to the male threads (12) at one end of central bar (10) and a hollow reservoir ball (320) is threadingly attached via female threads (325) of recess (323) to the male threads (12) at the other end of central bar (10). In this embodiment, the reservoir cavity (330) of reservoir ball (320) provides a reservoir in which a substance can be stored. When this tongue stud is in place in a wearers tongue or mouth, saliva from the wearer may enter side holes (17) and openings (250) to help dissolve any substance stored in the contiguous cavity comprising reservoir cavity (330), hollow core (15) and central core (230). Furthermore, this tongue stud may preferentially dispense the substance stored in the contiguous cavity either above or below the tongue depending on the location of the hollow ball (220). Specifically, when the hollow ball (220) is positioned above the tongue, then the substance is preferentially dispensed above the tongue because the openings (250) are positioned above the tongue. Likewise, when the hollow ball (220) is positioned below the tongue, then the substance is preferentially dispensed below the tongue because the openings (250) are positioned below the tongue. It is noted that hollow ball (220) may have only one opening (250) or may have a plurality of openings (250), the number of openings (250) merely affecting the rate at which a substance can be dispensed from tongue stud (300). Lastly as in the previous embodiments, when the substance to be dispensed is a liquid, then a foam insert can be placed inside of the contiguous cavity of the tongue stud (300). The foam insert may be placed in the entire contiguous cavity or only in a portion of the contiguous cavity such as shown in FIG. 5 by foam inserts (19) and (390). The foam insert provides a means for retaining the liquid so that the liquid diffuses over time out of the central core (230) into the wearer's mouth.

Figure 7:
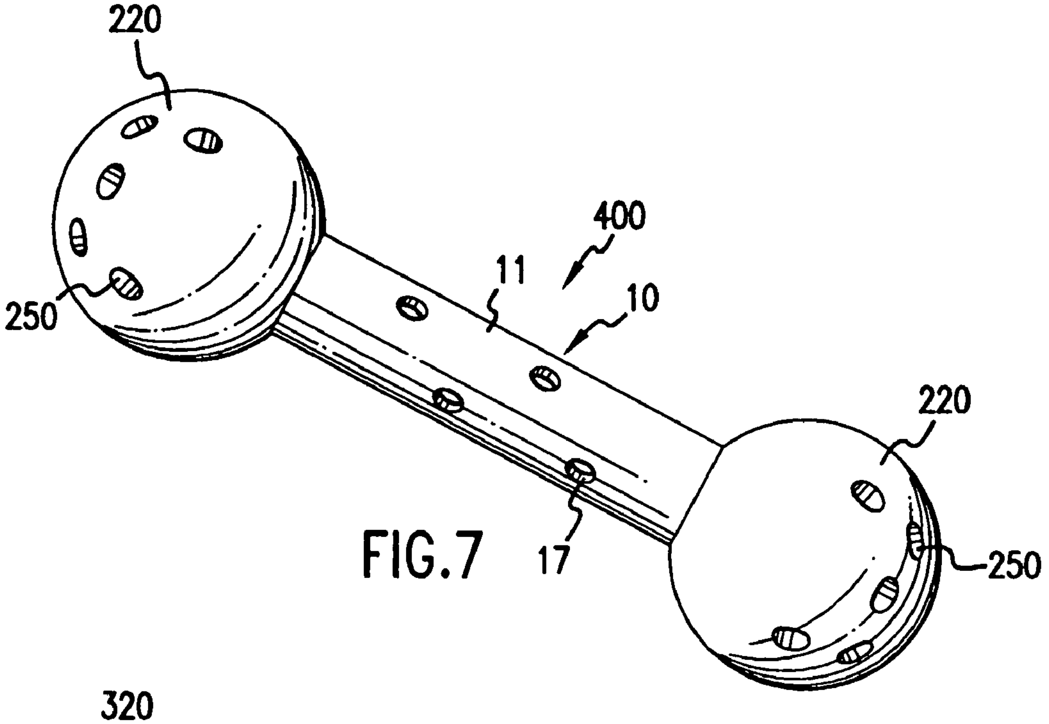
FIG. 7 illustrates a side view of tongue stud (400) having the means for dispensing a substance formed within two hollow balls and the central bar.

FIG. 7 illustrates another embodiment of the invention. This tongue stud (400) comprises of hollow balls (220) threadingly attached at each end of central bar (10). This embodiment provides a means for quickly dispensing a substance contained within the tongue stud (400). It is noted that each hollow ball (220) could have only one opening (250) or a plurality of openings (250). It is also possible to construct the invention such that each hollow ball (220) has a different number of openings without diverging from the scope of the invention.

Figure 8:
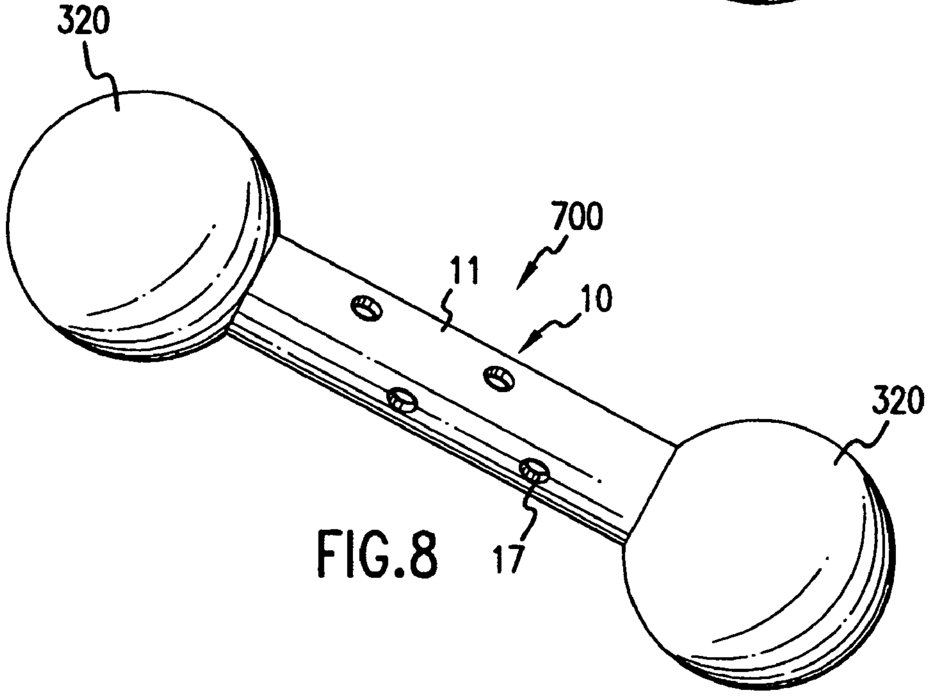
FIG. 8 illustrates a side view of tongue stud (700) having the means for dispensing a substance formed within two reservoir balls and the central bar.

FIG. 8 illustrates another embodiment of the invention. This tongue stud (700) comprises of reservoir balls (320) threadingly attached at each end of central bar (10). This embodiment provides a means for slowly dispensing a substance contained within the tongue stud (700).

Figure 9:
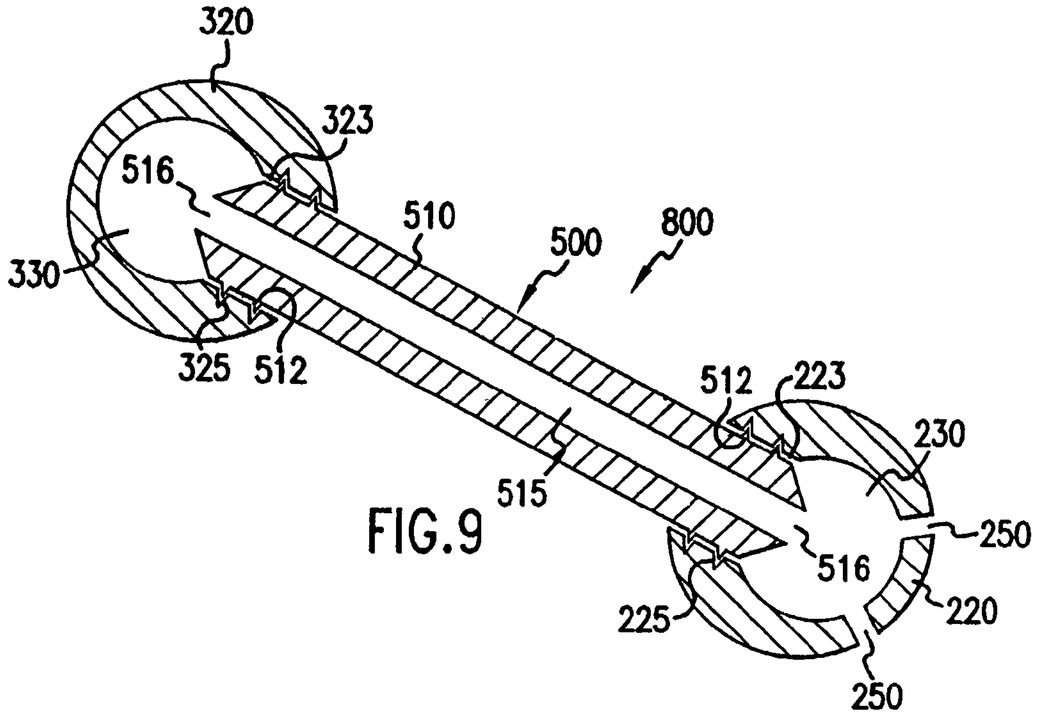
FIG. 9 illustrates a cross sectional view of tongue stud (800) having the means for dispensing a substance formed within a reservoir ball, a hollow ball, and a central bar wherein the central bar has no side openings.
Figure 10:
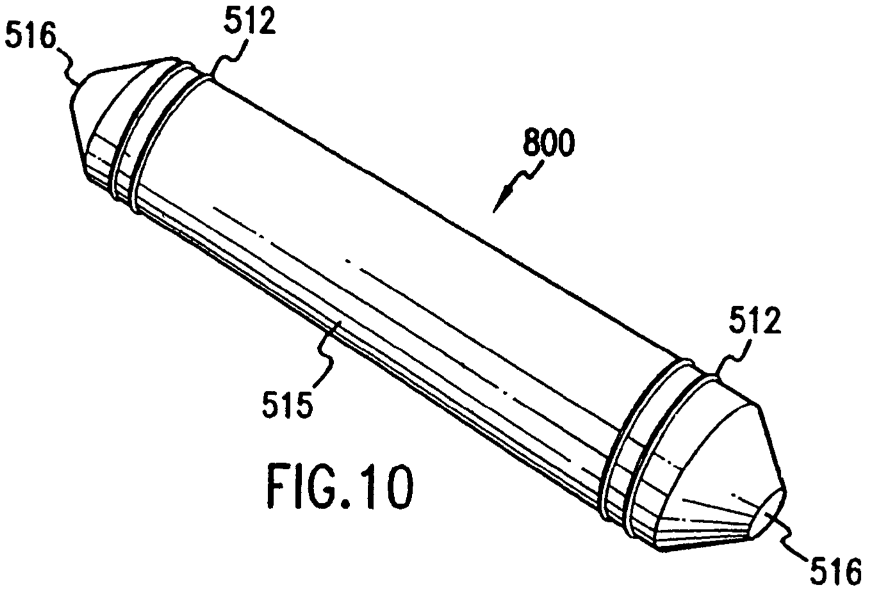
FIG. 10 illustrates a side view of the central bar having no side openings.
Figure 11:
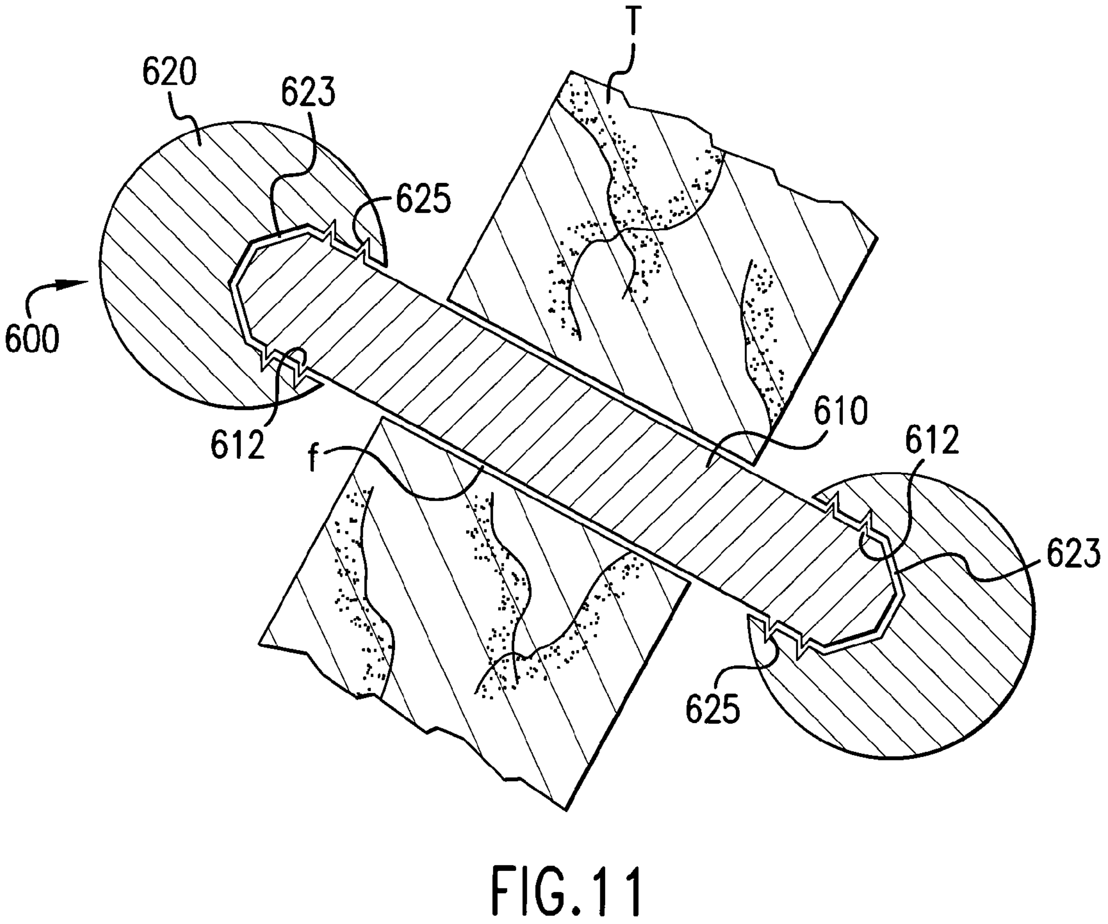
FIG.11 PRIOR ART
FIG. 11 illustrates a cross sectional view of the prior art tongue stud in place in a wearer's tongue.

FIGS. 9 and 10 illustrates another preferred embodiment of the invention. In this embodiment, the tongue stud (800) comprises of central bar (500) that has male threads (512) at each end and a hollow core (515) that is a hollow cavity having end openings (516) at each end of the central bar (500). It is noted that central bar (500) has a side wall (510) that has no side openings. At one end of central bar (500) a reservoir ball (320) is threadingly attached via female threads (325) of recess (323) to the male threads (512) of central bar (500). At the other end of central bar (500) a hollow ball (220) is threadingly attached via female threads (225) of recess (223) to the male threads (512) of central bar (500). In this embodiment, reservoir cavity (330), hollow core (515), and central core (230) form one large contiguous cavity that is capable of storing and dispensing a substance into a wearer's mouth via openings (250). Clearly, this embodiment would preferentially dispense a substance contained within the large contiguous cavity from the hollow ball (220) which has one or more openings (250); therefore, when the tongue stud is in place in a wearer's tongue the substance would be preferentially dispensed above the tongue when the tongue stud is worn with the hollow ball (220) positioned above the tongue. Likewise, the substance would be preferentially dispensed below the tongue when the tongue stud is worn with the hollow ball (220) positioned below the tongue. It is noted that tongue stud (800) can be placed elsewhere in the mouth such as in a fistula formed in the wearer's lower lip. The tongue stud (800) would be positioned with the hollow ball (220) positioned inside the mouth so that the substance would be dispensed into the wearer's mouth without leaking the substance onto the outer lip. Lastly, it is noted that as in previous embodiments of the invention, a foam insert could be placed inside the large contiguous cavity when the substance to be dispensed is a liquid.

It is noted that it is within the scope of the present invention to create other tongue stud embodiments by combining either central bar (10), central bar (100), central bar (500) or central bar (610) with any one of hollow ball (220), reservoir ball (320), or solid ball (620) attached to one end of the bar and with any one of hollow ball (220), reservoir ball (320), or solid ball (620) attached to the other end of the bar. The only permutation taught by the prior art is the combination of central bar (610) with two solid balls (620), but this is the prior art tongue stud which is not capable of dispensing a substance. Furthermore, it is noted that the present invention is not limited to the geometry illustrated. Clearly, the bars may be curved or corkscrew in shape and the balls may be disk, block, or pyramid in shape without departing from the spirit of the invention.

The hollow balls (220) and (320) and the solid balls (620) are merely illustrative and are not meant to limit the geometry of the invention. More generically, the balls (220), (320) and (620) are end members that can have any practical geometry. Some non-limiting examples of the geometry of the end members include spherical shapes, disk shapes, square shapes, polygonal shapes, cylinder shapes, pyramidal shapes and donut shapes.

It is asserted that the tongue stud embodiments evinced herein in the drawings and the specification are merely illustrations of the preferred embodiments of the invention and its principal variations, and are not meant to be limiting or restrictive, the full spirit and scope of the invention being further defined by the appended claims.

The invention claimed is:

1. A method for dispensing a substance into a mouth, wherein the substance is selected from the group consisting of a breath freshener and a flavoring agent, the method comprising the steps of:

providing a mouth and tongue stud including a means for dispensing a substance formed in a portion of the stud, wherein the means for dispensing a substance contains the substance and wherein the stud further comprises a bar having ends, a first end member attached to one end of the bar and a second end member attached to an other end of the bar, and the first end member removably attaches to the one end of the bar;

mounting the bar of the stud in a fistula formed in a wearer's tongue; and dispensing the substance into the wearer's mouth, wherein the substance is dispensed on or below, or on and below, the wearer's tongue solely by dissolving the substance over time in the wearer's saliva so that the dissolved substance is free to flow from the means for dispensing to on or below, or on and below, the wearer's tongue.

2. A method as recited in claim 1, wherein the substance comprises a breath freshener.

3. A method as recited in claim 2, wherein a medication is mixed with the breath freshener.

4. A method as recited in claim 2, wherein the bar is a solid bar that is without an internal cavity, and the means for dispensing a substance is formed in the second end member.

5. A method as recited in claim 1, wherein the substance comprises a flavoring agent.

6. A method as recited in claim 5, wherein the substance includes a breath freshener mixed with the flavoring agent.

7. A method as recited in claim 6, wherein a medication is mixed with the breath freshener and the flavoring agent.

8. A method as recited in claim 5, wherein a medication is mixed with the flavoring agent.

9. A method for dispensing a substance into a mouth, wherein the substance is a medication, the method comprising the steps of:

providing a mouth and tongue stud including a means for dispensing a substance formed in a portion of the stud, wherein the means for dispensing a substance contains the medication and wherein the stud comprises a bar having ends, a first end member attached to one end of the bar and a second end member attached to an other end of the bar, and the first end member removably attaches to the one end of the bar;

mounting the bar of the stud in a fistula formed in a wearer's tongue; and dispensing the medication into the wearer's mouth, wherein the substance is dispensed on or below, or on and below, the wearer's tongue solely by dissolving the substance over time in the wearer's saliva so that the dissolved substance is free to flow from the means for dispensing to on or below, or on and below, the wearer's tongue.

10. A method as recited in claim 9, wherein the bar is a solid bar that is without an internal cavity, and the means for dispensing a substance is formed in the second end member.

11. A method for dispensing a substance into a mouth, wherein the substance is selected from the group consisting of a breath freshener and a flavoring agent, the method comprising the steps of:

providing a mouth and tongue stud including a means for dispensing a substance formed in a portion of the stud, wherein the means for dispensing a substance contains the substance and wherein the stud comprises a bar having ends, a first end member attached to one end of the bar and a second end member attached to an other end of the bar, wherein the bar is a straight solid bar that is without an internal cavity and that is made of metal and the first end member removably attaches to the one end of the bar, and wherein the means for dispensing a substance is formed in one or both of the first end member and the second end member;

mounting the bar of the stud in a fistula formed in a part of a wearer's mouth; and dispensing the substance into the wearer's mouth, wherein the substance is dispensed on or below, or on and below, the wearer's tongue solely by dissolving the substance over time in the wearer's saliva.

12. A method for dispensing a substance into a mouth, wherein the substance is a medication, the method comprising the steps of:

providing a mouth and tongue stud including a means for dispensing a substance formed in a portion of the stud, wherein the means for dispensing a substance contains the medication and wherein the stud comprises a bar having ends, a first end member attached to one end of the bar and a second end member attached to an other end of the bar, wherein the bar is a straight solid bar that is without an internal cavity and that is made of metal and the first end member removably attaches to the one end of the bar, and wherein the means for dispensing a substance is formed in one or both of the first end member and the second end member;

mounting the bar of the stud in a fistula formed in a part of a wearer's mouth; and dispensing the medication into the wearer's mouth, wherein the medication is dispensed on or below, or on and below, the wearer's tongue solely by dissolving the medication over time in the wearer's saliva.

13. A method for dispensing a substance into a mouth, wherein the substance is selected from the group consisting of a breath freshener and a flavoring agent, the method comprising the steps of:

providing a mouth and tongue stud including a means for dispensing a substance formed in a portion of the stud, wherein the means for dispensing a substance contains the substance and wherein the stud further comprises a bar having ends, a first end member attached to one end of the bar and a second end member attached to an other end of the bar, and the first end member removably attaches to the one end of the bar, and wherein an insert is disposed in the means for dispensing a substance;

mounting the bar of the stud in a fistula formed in a wearer's tongue so that the first end member and the second end member hold the stud in the fistula; and dispensing the substance into the wearer's mouth, wherein the substance is dispensed into the wearer's mouth on or below, or on and below, the wearer's tongue by diffusing the substance from the stud into the wearer's mouth over time in the wearer's saliva.

14. A method as recited in claim 13, wherein the substance comprises a liquid.

15. A method for dispensing a substance into a mouth, wherein the substance is a medication, the method comprising the steps of:

providing a mouth and tongue stud including a means for dispensing a substance formed in a portion of the stud, wherein the means for dispensing a substance contains the substance and wherein the stud further comprises a bar having ends, a first end member attached to one end of the bar and a second end member attached to an other end of the bar, and the first end member removably attaches to the one end of the bar, and wherein an insert is disposed in the means for dispensing a substance;

mounting the bar of the stud in a fistula formed in a wearer's tongue so that the first end member and the second end member hold the stud in the fistula; and dispensing the substance into the wearer's mouth, wherein the substance is dispensed into the wearer's mouth on or below, or on and below, the wearer's tongue by diffusing the substance from the stud into the wearer's mouth over time in the wearer's saliva.

16. A method as recited in claim 15, wherein the substance comprises a liquid.

17. A method for dispensing a substance into a mouth, wherein the substance is selected from the group consisting of a breath freshener and a flavoring agent, the method comprising the steps of:

providing a mouth and tongue stud including a means for dispensing a substance formed in a portion of the stud, wherein the means for dispensing a substance contains the substance and wherein the stud further comprises a bar having ends, a first end member attached to one end of the bar and a second end member attached to an other end of the bar, and the first end member removably attaches to the one end of the bar;

mounting the bar of the stud in a fistula formed in a wearer's tongue so that the first end member and the second end member hold the stud in the fistula; and dispensing the substance into the wearer's mouth, wherein the substance has a form selected from the group consisting of a solid form and a tablet form and is dispensed on or below, or on and below, the wearer's tongue by dissolving the substance from the stud to flow on or below, or on and below, the wearer's tongue over time in the wearer's saliva.

18. A method as recited in claim 17, wherein the substance has a solid form and the solid form is a solid crystallized form.

19. A method for dispensing a substance into a mouth, wherein the substance is a medication, the method comprising the steps of:

providing a mouth and tongue stud including a means for dispensing a substance formed in a portion of the stud, wherein the means for dispensing a substance contains the substance and wherein the stud further comprises a bar having ends, a first end member attached to one end of the bar and a second end member attached to an other end of the bar, and the first end member removably attaches to the one end of the bar;

mounting the bar of the stud in a fistula formed in a wearer's tongue so that the first end member and the second end member hold the stud in the fistula; and dispensing the substance into the wearer's mouth, wherein the substance has a form selected from the group consisting of a solid form and a tablet form and is dispensed on or below, or on and below, the wearer's tongue by dissolving the substance from the stud to flow on or below, or on and below, the wearer's tongue over time in the wearer's saliva.

20. A method as recited in claim 19, wherein the substance has a solid form and the solid form is a solid crystallized form.

* * * * *